United States Patent
Dussarrat

(10) Patent No.: US 8,071,163 B2
(45) Date of Patent: Dec. 6, 2011

(54) DEPOSITION OF TA- OR NB-DOPED HIGH-K FILMS

(75) Inventor: Christian Dussarrat, Wilmington, DE (US)

(73) Assignee: L'Air Liquide Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 863 days.

(21) Appl. No.: 12/099,027

(22) Filed: Apr. 7, 2008

(65) Prior Publication Data

US 2008/0286983 A1    Nov. 20, 2008

Related U.S. Application Data

(60) Provisional application No. 60/910,522, filed on Apr. 6, 2007.

(51) Int. Cl.
*C23C 16/00* (2006.01)
*C23C 16/40* (2006.01)

(52) U.S. Cl. .......... 427/248.1; 427/255.11; 427/255.15; 427/255.19; 427/255.23

(58) Field of Classification Search ............... 427/248.1, 427/255.11, 255.15, 255.19, 255.23
See application file for complete search history.

(56) References Cited

U.S. PATENT DOCUMENTS

| | | | | |
|---|---|---|---|---|
| 5,677,002 | A * | 10/1997 | Kirlin et al. ................ | 427/248.1 |
| 6,623,656 | B2 * | 9/2003 | Baum et al. ............ | 252/62.9 PZ |
| 7,323,581 | B1 * | 1/2008 | Gardiner et al. ................ | 556/32 |
| 2002/0140005 | A1 | 10/2002 | Chung et al. | |
| 2004/0187778 | A1 | 9/2004 | Gros-Jean et al. | |
| 2006/0024975 | A1 * | 2/2006 | Ahn et al. ................... | 438/778 |
| 2006/0040480 | A1 | 2/2006 | Derderian et al. | |
| 2006/0148180 | A1 | 7/2006 | Ahn et al. | |

FOREIGN PATENT DOCUMENTS

| | | |
|---|---|---|
| EP | 1 146 141 | 10/2001 |
| EP | 1146141 A2 * | 10/2001 |
| EP | 1 427 005 | 6/2004 |
| WO | WO 2007 000186 | 1/2007 |
| WO | WO 2007 140813 | 12/2007 |

OTHER PUBLICATIONS

Ohshita, Y. et al., *Tris-diethylamino-silane decomposition due to tetrakis-diethylamino-hafnium in $Hf_{1-x}Si_xO_2$ chemical vapor deposition*, Jpn. J. Appl. Phys. vol. 42, No. 6A, pp. L578-L580, Jun. 2003.
Hendrix, B.C. et al., *Composition control of $Hf_{1-x}Si_xO_2$ films deposited on the by chemical-vapor deposition using amide precursors.*
Zhoa, C. et al. *Properties of HfTaxOy high-k layers deposited by ALCVD*, Electrochem Soc Proc vol. 2005-05, 133, 2005.
Yu, et al., *Electrical characteristics and a suppressed boron penetration behavior of thermally stable HfTaO gate dielectrics with polycrystalline-silicon gate*, Appl. Phys. Lett., 2893, 85, 2004.

* cited by examiner

*Primary Examiner* — Timothy Meeks
*Assistant Examiner* — Kelly M Gambetta
(74) *Attorney, Agent, or Firm* — Patricia E. McQueeney

(57) ABSTRACT

Methods and compositions for depositing high-k films are disclosed herein. In general, the disclosed methods utilize precursor compounds comprising Ta or Nb. More specifically, the disclosed precursor compounds utilize certain ligands coupled to Ta and/or Nb such as 1-methoxy-2-methyl-2-propanolate (mmp) to increase volatility. Furthermore, methods of depositing Ta or Nb compounds are disclosed in conjunction with use of Hf and/or Zr precursors to deposit Ta-doped or Nb-doped Hf and/or Zr films. The methods and compositions may be used in CVD, ALD, or pulsed CVD deposition processes.

18 Claims, No Drawings

DEPOSITION OF TA- OR NB-DOPED HIGH-K FILMS

CROSS-REFERENCE TO RELATED APPLICATIONS

The present application claims the benefit of U.S. Provisional Application Ser. No. 60/910,522, filed Apr. 6, 2007, herein incorporated by reference in its entirety for all purposes.

BACKGROUND

1. Field of the Invention

This invention relates generally to the field of semiconductor fabrication. More specifically, the invention relates to compositions and methods for semiconductor film deposition of Ta or Nb doped high-k materials.

2. Background of the Invention

With the dramatic shrinkage in new semiconductor based-devices, one of the most concerning issues of scaling metal-oxide-semiconductor field effect transistors (MOSFETs) is the increase of gate leakage current by direct tunneling because the thickness of silicon dioxide ($SiO_2$) gate insulators cannot be reduced further than about 1 nm. Silicon dioxide has been used as a gate oxide material for decades. As transistors have decreased in size, the thickness of the silicon dioxide gate dielectric has steadily decreased to increase the gate capacitance and thereby drive current and device performance. As the thickness scales below 2 nm, leakage currents due to tunneling increase drastically, leading to unwieldy power consumption and reduced device reliability. Replacing the silicon dioxide gate dielectric with a high dielectric constant (high-k) material allows increased gate capacitance without the concomitant leakage effects.

Hafnium silicate and hafnium silicon oxynitride have been regarded as some of the most promising high-k materials to replace silicon dioxide. The inclusion of silicon and nitrogen theoretically prevents the formation and the diffusion of SiO gas at the high-k/substrate interface. The most popular alternative to hafnium silicate and hafnium silicon oxynitride has been $HfAlO_x$ films.

Another approach is to form $HfTaO_x$ films by alternative pulses (ALD mode) of a Hf precursor, $H_2O$ (or another O source), a Ta precursor, $H_2O$ again these pulses being separated by an appropriate purge by an inert gas (this sequence forms one cycle which will be typically repeated several thousand times). As a result, the substrate surface is OH terminated after each $H_2O$ pulse and the Hf or Ta precursors, if suitable, react with the surface in the following pulse. Nevertheless, tantalum suffers because of its very limited volatility. The most popular tantalum alkoxide, polyethylene terephthalate (PET) $Ta(OEt)_5$ is volatile only above 130° C. However, for thin film deposition vaporization temperatures higher than 150° C. are generally required. The lack of volatility of these compounds is mainly due to the dimer structure of the molecule. Using higher alkoxides will not lead to a significantly more volatile molecule as an additional carbon atom on each of the ligand would increase the molecular weight. As such, there are no known solutions to adequately deposit HfTaO or HfFaON with chemical precursors using current deposition techniques such as chemical vapor deposition (CVD), pulsed CVD or atomic layer deposition (ALD).

Consequently, there is a need for methods and compositions for deposition of metal-TaO and/or metal-TaON for semiconductor fabrication.

BRIEF SUMMARY

Methods and compositions for depositing high-k films are disclosed herein. In general, the disclosed methods utilize precursor compounds comprising Ta or Nb. More specifically, the disclosed precursor compounds utilize certain ligands coupled to Ta and/or Nb such as 1-methoxy-2-methyl-2-propanolate (mmp) to increase volatility. Furthermore, methods of depositing Ta or Nb compounds are disclosed in conjunction with use of Hf and/or Zr precursors to deposit Ta-doped or Nb-doped Hf and/or Zr films. Other aspects of the methods and compositions will be described in more detail below.

In an embodiment, a method for depositing a high-k film on to one or more substrates comprises introducing a first metal precursor into the reaction chamber. The first metal precursor comprises a compound having the formula: $M^1(OR)_4L^1$. $M^1$ comprises Ta and Nb. R is an alkyl group, and $L^1$ has the formula, $-O-(CR^1R^2)_n-X-(R^3)(R^4)$ or $-NR^0-(CR^1R^2)_n-X-(R^3)(R^4)$, where $R^0$ is a hydrogen atom, or an alkyl group having 1 to 4 carbon atoms. $R^1$ and $R^2$ may each independently be a hydrogen atom, a methyl group, or an ethyl group. The subscript "n" is an integer ranging from 0 and 3, X is an O or N atom. $R^3$ is a hydrogen atom, or an alkyl group having from 1 to 4 carbon atoms, and $R^4$ is a hydrogen atom, or an alkyl group having 1 to 4 carbon atoms. $R^{0-4}$ may be the same or different from one another. The first metal precursor may additionally comprise a compound having the formula: $M^1(NR^1R^2)(NR^3R^4)(NR^5R^6)(NR^7R^8)(NR^9R^{10})$. $M^1$ comprises Ta or Nb. $R^{0-10}$ may each independently be an alkyl group having from 1 to 6 carbon atoms, and $R^{0-10}$ may be the same or different from one another. Moreover, the first metal precursor may be a compound having the formula: $M^1(=NR^0)(-NR^1R^2)(-NR^3R^4)(-NR^5R^6)$, where $R^{0-6}$ may each independently be an alkyl group having from 1 to 6 carbon atoms, and $R^{0-6}$ may be the same or different from one another. The first metal precursor may also be a compound having the formula: $M^1(X)_5, S(R^1R^2)$. $M^1$ is Ta or Nb. X is a halogen, and $R^1$ and $R^2$ may each independently be an alkyl group having 1 to 4 carbon atoms. The first metal precursor may further be any combinations of the above compounds. The method further comprises introducing a second metal precursor into a reaction chamber. The second metal precursor comprises hafnium or zirconium. The reaction chamber contains the one or more substrates. In addition, the method comprises vaporizing the first metal precursor and the second metal precursor to deposit the high-k film on to the one or more substrates.

In an embodiment, a precursor for the deposition of a high-k film comprises a compound having the formula: $M^1(OR)_4L^1$. $M^1$ comprises Ta and Nb. R is an alkyl group, and $L^1$ has the formula, $-O-(CR^1R^2)_n-X-(R^3)(R^4)$ or $-NR^0-(CR^1R^2)_n-X-(R^3)(R^4)$, where $R^0$ is a hydrogen atom, or an alkyl group having 1 to 4 carbon atoms. $R^1$ and $R^2$ may each independently be a hydrogen atom, a methyl group, or an ethyl group. The subscript "n" is an integer ranging from 0 and 3, X is an O or N atom. $R^3$ is a hydrogen atom, or an alkyl group having from 1 to 4 carbon atoms, and $R^4$ is a hydrogen atom, or an alkyl group having 1 to 4 carbon atoms. $R^{0-4}$ may be the same or different from one another. The precursor may also comprise a compound having the formula: $M^1(NR^1R^2)(NR^3R^4)(NR^5R^6)(NR^7R^8)(NR^9R^{10})$. $M^1$ comprises Ta or Nb. $R^{0-10}$ may each independently be an alkyl group having 1 to 6 carbon atoms, and $R^{0-10}$ may be the same or different from one another. Furthermore, the precursor may be a compound having the formula: $M^1(=NR^0)(-NR^1R^2)(-NR^3R^4)(-NR^5R^6)$, where $R^{0-6}$ may each independently be an alkyl group having from 1 to 6 carbon atoms, and $R^{0-6}$ may be the same or different from one another. In addition, the precursor may be a compound having the formula: $M^1(X)_5$, $S(R^1R^2)$. $M^1$ is Ta or Nb. X is a halogen, and $R^1$ and $R^2$ may each independently be an alkyl group having 1 to 4 carbon atoms. The first metal precursor may further be any combinations of the above compounds.

The disclosed precursor compounds may have higher volatility than existing precursor compounds. Increased volatility expedites the deposition of the high-k compounds as a film. The higher volatility is also advantageous in process such as ALD because more volatile precursors are easier to purge.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

Notation and Nomenclature

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections.

As used herein, the abbreviation "mmp" refers to 1-methoxy-2-methyl-2-propanolate [OCMe$_2$CH$_2$OMe]. Further, the abbreviation "Me" refers to a methyl (CH$_3$—) group, the abbreviation "Et" refers to an ethyl (CH$_4$CH$_2$—) group, and the abbreviation "Bu" refers to a butyl group. The abbreviation "t-Bu" refers to a tertiary butyl group.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

DETAILED DESCRIPTION OF THE PREFERRED EMBODIMENTS

In an embodiment, a precursor for the deposition of high-k film comprises a compound having the formula: $M^1(OR)_4L^1$. $M^1$ may be a Group VB metal. Preferably, $M^1$ is Ta or Nb. R is preferably an alkyl group such as without limitation, Me or Et. However, R may be an alkyl group with any number of carbon atoms. $L^1$ is a chelating ligand or group for increasing the volatility of the precursor for deposition purposes. The chelating group may be of the form —O—(CR$^1$R$^2$)$_n$—X—(R$^3$)(R$^4$) or —NR$^0$—(CR$^1$R$^2$)$_n$—X—(R$^3$)(R$^4$) where $R^0$ comprises hydrogen, or a alkyl group having from 1 to 4 carbon atoms. The alkyl groups may be branched, linear, or cyclic. In addition, $R^1$ and $R^2$ may each independently be a hydrogen group, a methyl group, or an ethyl group. The subscript "n" may be an integer ranging from 0 and 3. X is an O or N atom. $R^3$ may be a hydrogen group, or a linear, cyclic or branched alkyl group having from 1 to 4 carbon atoms. $R^4$ may be a hydrogen group, or a linear, cyclic or branched alkyl group having from 1 to 4 carbon atoms. $R^{0-4}$ may be the same or different from one another. According to one embodiment, the precursor may be Ta(OMe)$_4$(mmp). Other examples of the precursor include without limitation, Nb(OMe)$_4$(mmp), Ta(OEt)$_4$(mmp), and Nb(OEt)$_4$(mmp).

The precursor may be prepared with any processes known to those of skill in the art. For example, Ta(OMe)$_4$(mmp) can be prepared from the addition of mmp-H to a stirred solution containing Ta(OMe)$_5$ (the molar ratio between Ta(OMe)$_5$ and mmpH may be 1:1). After stirring, the solution may be set to reflux. The solvent may then removed in vacuo and the pure compound may obtained after vacuum distillation.

The precursor is designed so that embodiments of the precursor are more volatile than existing Ta/Nb precursors such as dimeric Ta(OMe)$_5$ or Ta(OEt)$_5$. Without being limited by theory, the disclosed precursors may be more volatile than the dimeric precursors by promoting a monomeric form. Accordingly, embodiments of the precursor are preferably liquid at room or at moderate temperature (i.e. lower than vaporization temperature). Generally, embodiments of the precursor may have a vaporization temperature ranging from about room temperature to about 200 C alternatively from about 50 C to about 150 C.

In an alternative embodiment, the precursor may be a metal amide having the formula $M^1(NR^1R^2)(NR^3R^4)(NR^5R^6)(NR^7R^8)(NR^9R^{10})$. $M^1$ is the same as disclosed above (e.g. Ta, Nb, etc.). $R^{1-10}$ may each independently be methyl or ethyl groups. Alternatively, embodiments of the precursor may have mixed amidoimido ligands such as $M^1(=NR^0)(-NR^1R^2)(-NR^3R^4)(-NR^5R^6)$ where $R^{0-6}$ may be linear, branched or cyclic alkyl groups having from 1 to 6 carbon atoms. In specific embodiments, $R^{0-6}$ may each independently be a methyl group or an ethyl group. $R^{0-6}$ may be the same or different from one another. In an exemplary embodiment, the precursor is Ta(=N-t-Bu)(NEt$_2$)$_3$.

In yet another embodiment, the precursor may be a compound having the formula $M^1(X)_5$, $S(R^1R^2)$. $M^1$ may be a Group VB metal. Preferably, $M^1$ is Ta or Nb. X is a halogen such as without limitation, Cl, Br, F, etc. $R^1$ and $R^2$ may each independently be a linear, branched or cyclic alkyl group having from 1 to 4 carbon atoms. $R^1$ and $R^2$ may be the same or different from one another. In an exemplary embodiment, the precursor may be a TaCl$_5$, S(Et)$_2$ adduct.

The disclosed precursor compounds may be deposited using any deposition methods known to those of skill in the art. Examples of suitable deposition methods include without limitation, conventional CVD, low pressure chemical vapor deposition (LPCVD), atomic layer deposition (ALD), pulsed chemical vapor deposition (P-CVD), plasma enhanced atomic layer deposition (PE-ALD), or combinations thereof. In an embodiment, a first metal precursor and a second metal precursor may be introduced into a reaction chamber. The reaction chamber may be any enclosure or chamber within a device in which deposition methods take place such as without limitation, a cold-wall type reactor, a hot-wall type reactor, a single-wafer reactor, a multi-wafer reactor, or other types of deposition systems under conditions suitable to cause the precursors to react and form the layers.

Generally, the reaction chamber contains one or more substrates on to which the high-k layers or films will be deposited. The one or more substrates may be any suitable substrate used in semiconductor manufacturing. Examples of suitable substrates include without limitation, silicon substrates, silica substrates, silicon nitride substrates, silicon oxy nitride substrates, tungsten substrates, or combinations thereof. Additionally, substrates comprising tungsten or noble metals (e.g. platinum, palladium, rhodium or gold) may be used.

The first metal precursor may be any of the Ta/Nb precursors described above. The second metal precursor may be a compound having the formula: $M^2(L^2)(L^3)(L^4)(L^5)$. $M^2$ may be a Group IVB metal including without limitation, Hf, Zr, etc. $L^{2-5}$ may each independently be any suitable group including without limitation, a halogen, amide groups, alkoxide groups, nitrate groups. In particular, suitable groups also include without limitation, Cl, NMeEt, NMe$_2$, NEt$_2$, NO3, or O-t-Bu. $L^{2-5}$ may be the same or different from on another. The ratio of the second metal precursor to the first metal precursor introduced into the reaction chamber may range from about 100:1 to about 1:100, alternatively from about 1:1 to about 10:1.

In embodiments, the reaction chamber may be maintained at a pressure ranging from about 0.1 Torr to about 1000 Torr. In addition, the temperature within the reaction chamber may range from about 300° C. to about 700° C. Furthermore, the deposition of the high-k film may take place in the presence of an oxidizing gas or an oxygen source. Examples of suitable gases include without limitation, oxygen, ozone, hydrogen peroxide, nitric oxide, nitrous oxide, or combinations thereof. In addition, the deposition of the high-k film may take place in the presence of a nitridizing (i.e. a nitrogen containing gas) gas such as without limitation, ammonia, hydrazine, substituted alkylhydrazines, amines, nitric oxide, nitrous oxide, or combinations thereof. It is contemplated that both an oxidizing gas and a nitridizing gas may be introduced into the reaction chamber. In further embodiments, an inert gas may be introduced into the reaction chamber. Examples of inert gases include without limitation, He, Ar, Ne, or combinations thereof.

The first and second metal precursors may be introduced sequentially (as in ALD) or simultaneously (as in CVD) into the reaction chamber. In one embodiment, the first and second metal precursors may be pulsed sequentially or simultaneously (e.g. pulsed CVD) into the reaction chamber while the oxidizing or nitridizing gas is introduced continuously into the reaction chamber. Each pulse of the first and/or second metal precursor may last for a time period ranging from about 0.01 s to about 10 s, alternatively from about 0.1 s to about 5 s, alternatively from about 1 s to about 3 s. In another embodiment, the oxidizing gas and/or the nitridizing gas may also be pulsed into the reaction chamber. In such embodiments, the pulse of each gas may last for a time period ranging from about 0.01 s to about 10 s, alternatively from about 0.1 s to about 5 s, alternatively from about 1 s to about 3 s.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present to invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A method for depositing a high-k film on to one or more substrates comprising:
   a) introducing a first metal precursor into the reaction chamber, wherein the first metal precursor comprises a compound having the formula selected from the group consisting of:

wherein $M^1$ is selected from the group consisting of Ta and Nb, R is an alkyl group, and $L^1$ has the formula, —O—(CR$^1$R$^2$)$_n$—X—(R$^3$)(R$^4$) or —NR$^0$—(CR$^1$R$^2$)$_n$—X—(R$^3$)(R$^4$), wherein $R^0$ is a hydrogen atom, or an alkyl group having 1 to 4 carbon atoms, $R^1$ and $R^2$ may each independently be a hydrogen atom, a methyl group, or an ethyl group, n is an integer ranging from 0 and 3, X is an O or N atom, $R^3$ is a hydrogen atom, or an alkyl group having from 1 to 4 carbon atoms, and $R^4$ is a hydrogen atom, or an alkyl group having 1 to 4 carbon atoms, and wherein $R^{0-4}$ may be the same or different from one another,
   a compound having the formula:

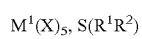

wherein $M^1$ is Ta or Nb, X is a halogen, and $R^1$ and $R^2$ may each independently be an alkyl group having 1 to 4 carbon atoms,
   and combinations thereof.
   b) introducing a second metal precursor into a reaction chamber, wherein the second metal precursor comprises hafnium or zirconium, and wherein the reaction chamber contains the one or more substrates; and
   c) vaporizing the first metal precursor and the second metal precursor to deposit the high-k film on to the one or more substrates.

2. The method of claim 1 wherein the second metal precursor has the formula: $M^2$ $(L^2)(L^3)(L^4)(L^5)$, wherein $M^2$ comprises hafnium or zirconium, $L^{2-5}$ comprises a halogen group, an amide group, an alkoxide group, or a nitrate group, and wherein $L^{2-5}$ may be the same or different from one another.

3. The method of claim 2, wherein $L^{2-5}$ may each independently comprise Cl, NMeEt, NMe$_2$, NEt$_2$, NO3, or O-t-Bu.

4. The method of claim 1 wherein (a) and (b) occur simultaneously.

5. The method of claim 1 wherein (a) and (b) occur sequentially.

6. The method of claim 1 wherein (a) and (b) comprise pulsing the first metal precursor and the second metal precursor into the reaction chamber.

7. The method of claim 6 wherein each pulse lasts for a time period ranging from about 0.01 s to about 10 s.

8. The method of claim 1, further comprising introducing one or more gases into the reaction chamber, wherein the one or more gases comprise an oxidizing gas, a nitridizing gas, an inert gas, or combinations thereof.

9. The method of claim 8 wherein the oxidizing gas comprises oxygen, ozone, hydrogen peroxide, nitric oxide, nitrous oxide, or combinations thereof.

10. The method of claim 8 wherein the nitridizing gas comprises ammonia, hydrazine, substituted alkylhydrazines, amines, nitric oxide, nitrous oxide, or combinations thereof.

11. The method of claim 8 wherein the one or more gases are pulsed into the reaction chamber.

12. The method of claim 11 wherein each pulse lasts for a time period ranging from about 0.01 s to about 10 s.

13. The method of claim 1 wherein the one or more substrates comprise silicon, silica, silicon nitride, silicon oxy nitride, tungsten, or combinations thereof.

14. The method of claim 1 wherein the reaction chamber is at a temperature ranging from about 300° C. to about 700° C. in (c).

15. The method of claim 1 wherein the reaction chamber is at a pressure ranging from about 0.01 Torr to about 10 Torr.

16. The method of claim 1 wherein the ratio of the second metal precursor to the first metal precursor ranges from about 100:1 to about 1:100.

17. The method of claim 1, wherein the first metal precursor is selected from the group consisting of $Ta(OMe)_4$(1-methoxy-2-methyl-2-propanolate), $Nb(OMe)_4$(1-methoxy-2-methyl-2-propanolate), $Ta(OEt)_4$(1-methoxy-2-methyl-2-propanolate), and $Nb(OEt)_4$(1-methoxy-2-methyl-2-propanolate).

18. The method of claim 1, wherein the first metal precursor is $TaCl_5$, $S(Et)_2$.

* * * * *